United States Patent [19]

MacNeil

[11] Patent Number: 5,194,387
[45] Date of Patent: Mar. 16, 1993

[54] PROCESS FOR THE INCORPORATION OF DNA MOLECULES INTO MICROORGANISMS WITH METHYL-SPECIFIC RESTRICTION SYSTEMS

[75] Inventor: Douglas J. MacNeil, Westfield, N.J.

[73] Assignee: Merck & Co., Inc., Rahway, N.J.

[21] Appl. No.: 792,998

[22] Filed: Nov. 15, 1991

Related U.S. Application Data

[63] Continuation of Ser. No. 192,035, May 9, 1988, abandoned.

[51] Int. Cl.$^5$ .............................................. C12N 15/70
[52] U.S. Cl. .............................. 435/320.1; 435/252.33
[58] Field of Search ................ 435/172.3, 320.1, 193, 435/199, 886, 252.33; 935/55, 56

[56] References Cited

U.S. PATENT DOCUMENTS

4,710,466 9/1984 Hershberger et al. ................ 435/91

FOREIGN PATENT DOCUMENTS

118367 9/1984 European Pat. Off. .
147145 12/1984 European Pat. Off. .
176340 9/1985 European Pat. Off. .
238324 9/1987 European Pat. Off. .
248678 12/1987 European Pat. Off. .
281356 9/1988 European Pat. Off. .

OTHER PUBLICATIONS

Hershey, R. M. (1984) Nature 311, 580-581.
Cox et al., J. Bacteriology 159 p. 499-504 (1984).
Matsushima et al, Mol. Gen. Genet 206 pp. 393-400 (1987).
Kessler et al, Gene pp. 1-8 (1986).
Sladek et al., J. Bacteriology 165 pp. 219-225 (1986).
Raleigh et al., Proc. Nat. Acad. Sci. USA pp. 9070-9074 (1986).
Bailey et al., J. Gen. Microbiology 132 pp. 2945-2947 (1986).
Okanishi et al, J. Gen. Microbiology 80 p. 389-400 (1974).
Foor et al, Gene 39 pp. 11-16 (1985).

Bolivar et al. Gene 2 pp. 95-113 (1977).
Holmes et al, Analytical Biochemistry 114 pp. 193-197 (1981).
Clewell et al, J. of Bacteriology 110 pp. 1135-1146 (1972).
Thompson et al, (I), J. Bacteriology 151 pp. 668-677 (1982).
Thompson et al (II), Gene 20 pp. 51-62 (1982).
Hopwood et al (I), Genetic Manipulation of Streptomyces—A Laboratory Manual pp. 1-14, 71-78, 104-109, 232-236 and 239 (1985).
Maniatis et al, Molecular Cloning—A Laboratory Manual pp. 98, 104-106, 146, 150-162, 249-251, 296-299, 437-455 and 458-469.
MacNeil et al (I), J. Indus-Microbiology 2 pp. 209-218 (1987).
MacNeil J. Microbiological Methods 5 pp. 115-123 (1986).

(List continued on next page.)

Primary Examiner—Charles L. Patterson, Jr.
Attorney, Agent, or Firm—Joseph F. DiPrima; David L. Rose

[57] ABSTRACT

There is disclosed a process for the incorporation of DNA into a microorganism that, because of natural restrictions in the organism, normally would prevent or limit the incorporation of the DNA. The process involves the selection of an intermediate host organism that has no restrictions to the incorporation of DNA. The DNA is then transferred into the intermediate host which is readily accomplished because there are no restrictions. The DNA is then isolated from the intermediate host and transferred into the target organism. Using this process the natural restrictions of the host organism are circumvented and DNA is transferred from a source organism to a target organism that normally would not be possible. In this manner desirable characteristics from the source organism can be imparted into the target organism.

1 Claim, 1 Drawing Sheet

OTHER PUBLICATIONS

Fisher et al, *Macrolide Antibiotics* pp. 553–606 (1984).
MacNeil et al (II), *Plasmid* 16 pp. 182–194 (1986).
Burg et al. *Antimicrobial Agents & Chemotherapy* (Mar. 1979) vol. 15 No. 3 pp. 361–361.
Roberts, *Nucleic Acids Research* 13 (Supp) pp. 165 (1985).
Mandell et al. *J. Mol. Biology* 53 pp. 159–162 (1970).
MacNeil, Abs. Pap. Am. Soc. Micro. 88 Abs. No. H-71 (1988).
Keiser, et al, Mol. Gen Genet, vol. 185, (1982) pp. 223–238.
Putter, et al Experientia 37, (1981) pp. 963–964.
Floss, Heinz G., Trends in Biotechnology, (1987) pp. 111–115.
Hopwood, et al, Nature vol. 314 (Apr. 1985) pp. 642–644.
Omura, Satoshi, et al Macrolide Antibiotics Chap. I (1984) pp. 3–29.
Miller, Jeffrey H. Experiments in Molecular Genetics (1972) p. 433.

FIG-1

PROCESS FOR THE INCORPORATION OF DNA MOLECULES INTO MICROORGANISMS WITH METHYL-SPECIFIC RESTRICTION SYSTEMS

This is a continuation of U.S. patent application Ser. No. 192,035, filed May 9, 1988, abandoned.

DESCRIPTION OF THE PRIOR ART

The introduction of foreign DNA, including plasmids, phages, and chromosomal DNA fragments, into microorganisms is a well established procedure. However, certain microorganisms cleave and inactivate foreign DNA through restriction systems making it difficult or impossible to introduce foreign DNA into these microorganisms. Restriction-modification systems are widespread in microorganisms. Most restriction-modification systems are composed of a methylase and an endonuclease. The modification enzyme (methylase) modifies the host DNA at a specific sequence composed of 4 or more bases, and the restriction endonuclease cleaves unmodified, foreign DNA at or near the specific sequence (for a review see Kessler et al. Gene 47 pg. 1-153 (1986)). Over 600 restriction endonucleases and 98 methylases are known. Three methyl-specific restriction systems have been described. In strains with methyl-specific restriction systems, foreign, methyl modified DNA is restricted and the host "modification" is the lack of modified DNA. Diplococcus pneumoniae restricts DNA containing $N^6$-methyladenine at the sequence GATC. Two other strains restrict DNA containing 5-methylcytosine, but these strains show little or no sequence specificity.

It is important to develop cloning systems and vectors for Streptomyces since microorganisms of that genus produce over seventy percent of all known antibiotics. Streptomyces avermitilis produces macrolide compounds, called avermectins, which are commercially important in the control of animal parasites. Avermectins are potent anthelmintic compounds which are active against many endoparasites of animals and humans, including Onchocerca volvulus the agent of onchocerciasis or "river blindness". The avermectins are also active against almost all arthropod ectoparasites and are effective in controlling numerous agricultural pests. Avermectins are an example of secondary metabolites produced during the stationary phase of growth in Streptomyces. Procedures to study the biosynthesis of secondary metabolites, using cloning vectors and recombinant DNA techniques, have been developed for several Streptomyces species. However, certain procedures can only be performed in Escherichia coli (i.e. the use of lambda vectors, cosmids, M13 sequencing vectors, transposon mutagenesis, and regulated expression vectors). To take advantage of the procedures available in E. coli, Streptomyces-E. coli shuttle vectors have been made. In order to isolate and study the genes involved in avermectin biosynthesis, cloning systems have been developed for S. avermitilis. Vectors have been constructed which include those derived from phage TG1 and plasmid pVE1 and an efficient transformation procedure has been developed. Unfortunately Streptomyces-E. coli shuttle vectors can not be introduced directly into S. avermitilis because S. avermitilis restricts the entry of DNA isolated from E. coli. This restriction barrier is a problem in any attempt to produce hybrid antibiotics in S. avermitilis by the introduction of biosynthetic genes from other microorganisms into S. avermitilis.

Previously, restriction barriers have been overcome in microorganisms by isolating mutants deficient in restriction. Many bacteria contain several restriction systems necessitating the sequential elimination of the restriction systems by mutation. This process is time consuming and must be repeated for each new strain.

A method has been described in European patent application 853,067,635 to overcome a cloning barrier in S. fradiae by passing modified Streptomyces DNA through an intermediate E. coli host. However, the E. coli described is methylase proficient, and DNA isolated form this strain would still be restricted by methyl specific restriction proficient strains.

Additional references which are pertinent to the instant invention are listed in Table 7.

SUMMARY OF THE INVENTION

Specifically it is an object to describe the process of transferring DNA which would be restricted by a microorganism into an intermediate host system and then reisolating the plasmid DNA from the intermediate host system and incorporating it into a microorganism. It is a still further object of this invention to describe the DNA which is isolated from a system with restrictions and is transferred into an intermediate host system and then into a microorganism. A still further object is to describe the intermediate host system. Further objects will become apparent from a reading of the following description.

This invention is concerned with a process for the incorporation of DNA into microorganisms that, because of the presence of methyl-specific restriction systems, would naturally prevent or limit the incorporation of DNA into the microorganisms. Specifically, many microorganisms have restriction systems which limit or prevent DNA containing N-methyladeneine or 5-methylyctosine from being incorporated therein. The instant process provides a novel method for the incorporation of DNA into microorganisms possessing methyl-specific restriction systems. Thus, it is an object of this invention to describe the process for incorporating DNA into microorganisms with methyl-specific restriction systems.

The process described here will have utility as a means of producing foreign DNA andor its products through replication of the microorganisms, or through the imparting of valuable properties to the cells by virtue of the presence of the foreign DNA therein.

DETAILED DESCRIPTION OF THE INVENTION AND PREFERRED EMBODIMENTS

Several derivatives of the broad host range Streptomyces plasmid pVE1 have been constructed (MacNeil et al. Plasmid 16 182-194 (1986)) and some of these derivatives could be useful as cloning vectors in S. avermitilis. One small, 4.9 kb derivative of pVE1 encoding thiostrepton-resistance, pVE28, can efficiently transform S. avermitilis to yield $10^7$ transformants per μg of DNA (MacNeil & Klapko, 1987). A potentially useful class of vectors for use in S. avermitilis would be shuttle vectors composed of E. coli and Streptomyces plasmids. These vectors would allow the application of many procedures developed in E. coli to S. avermitilis DNA. However, when a shuttle vector pVE3, a 15.4 kb cointegrant between pBR322 and pVE1, was isolated from *E. coli* and used to transform *S. avermiltilis*, no transformants were obtained. This same vector replicates in Streptomyces, since *S. lividans* protoplasts can be transformed by pVE3 DNA. Moreover, when pVE3 DNA was isolated from *S. lividans*, a streptomycete described as lacking any significant restriction, the pVE3 DNA could efficiently transform *S. avermitilis* protoplasts. These results suggest that *S. avermitilis* contains a restriction system. Since restriction of DNA during transformation is dependent on the presence of recognition sites for the host restriction enzyme, smaller plasmids often can be used to transform a particular strain. However, when a smaller, 7.5 kb shuttle vector, pVE328 was isolated from *E. coli* and used to transform *S. avermitilis*, it also was restricted.

The nature of restriction among *S. avermitilis*, *S. lividans*, and *E. coli* was investigated. DNA from the shuttle vectors pVE3 and pVE328 was prepared from *E. coli*, *S. lividans*, and *S. avermitilis* and 100 ng used to transform the three species. Table 2 shows the results of these experiments Both shuttle vectors showed a similar restriction pattern. *S. avermitilis* efficiently restricts DNA isolated from *E. coli*, reducing the transformation frequency more than $10^5$-fold. *S. lividans* also restricted the entry of DNA from *E. coli*, but only by 10-fold. No restriction was seen by *E. coli* of DNA isolated from either *S. avermitilis* or *S. lividans*.

RESTRICTION OF IN VIVO MODIFIED DNA BY *S. Avermitilis*

The restriction shown by *S. avermitilis* is not limited to DNA isolated from *E. coli*, but also restricts DNA from a modification proficient Streptomyces. This was determined by isolating DNA from *S. griseus*. *S. griseus* is a known host for pVE1 derivatives, although it restricts the entry of DNA from *S. avermitilis* and *S. lividans* (see Table 3). When *S. griseus* was transformed with pVE28, only a derivative, which was 0.4 kb smaller than pVE28, was isolated from the transformants. This deletion derivative was designated pVE614. When pVE614 is isolated from *S. griseus* it is resistant to cleavage by SstI. However, when pVE614 is isolated from *S. lividans*, it is cleaved by SstI at a single site, the parental plasmid pVE28 contains two SstI sites, but one site is within the 0.4 kb region deleted to form pVE614. Evidently, *S. griseus* contains a restriction-modification system which modifies the DNA that overlaps the SstI site. When pVE614 was isolated from *S. griseus* it could be used to transform *S. lividans*, but not *S. avermitilis*. This was due to restriction, rather than problems with the maintenance or replication of pVE614, because pVE614 DNA isolated from *S. lividans* will efficiently transform *S. avermitilis* (see Table 3). Thus, *S. avermitilis* contains a restriction system which restricts the entry of DNA from *E. coli* RR1, known to contain the dam and dcm modification systems, and from *S. griseus*, shown here to modify DNA at or near a SstI site in pVE614

DESCRIPTION OF THE DRAWING

FIG. 1 is a detailed restriction map of plasmid pVE328. The two primary cloning sites, BglII and HpaI, are indicated by **. Other unique sites in the plasmid that could be used for cloning and which do not interfere with any plasmid functions are the HindIII, BalI, and SstI sites. Seven regions of the plasmid include the Streptomyces plasmid replication region of pVE1 (S_rep), the *E. coli* plasmid replication region of pBR322 (E_rep), the ampicillin resistance region (Amp), the thiostrepton resistance region (Thio), two lambda cos regions (lamcos1 and lamcos2) and the TG1 cos region (TG1cos). Enzymes known not to cut the plasmid are also listed.

Restriction of in vitro Methylated DNA by *S. avermitilis*

Since *S. avermitilis* does not restrict DNA isolated from *S. lividans*, *S. lividans* must process DNA in one of two ways so that DNA is not cleaved by *S. avermitilis* restriction enzymes. *S. lividans*, a species unrelated to *S. avermitilis*, could coincidently modify the sites in DNA recognized by a *S. avermitilis* restriction-modification system. Alternatively, *S. avermitilis* might contain a methyl-specific restriction system and *S. lividans* might not methylate DNA. This latter possibility was tested by transforming *S. avermitilis* protoplasts with pVE28, a 4.9 kb, high copy number Streptomyces plasmid that was modified in vitro with various methylases. Table 4 shows that *S. avermitilis* strongly restricted DNA that was modified with AluI, dam, HhaI, HphI, and TaqI methylases, the efficiency of transformation (eot was reduced between $10^{-3}$ and $10^{-4}$. The 4 or 5 bp recognition sites for these methylases occur frequently in the DNA tested. pVE28 and other pVE1 derivatives with only 1, 2, or 3 sites for in vitro methylation were only weakly restricted since their efficiency of transformation was reduced only about 10 fold (see Table 4). This indicates that the probability of a DNA molecule being restricted by *S. avermitilis* is proportional to the number of methylated bases it contains. There appears to be no sequence specificity to the methyl-specific restriction observed in *S. avermitilis*, since all 8 methylases tested reduced the eot of the modified plasmids. *S. avermitilis* restricts both 5-methylcytosine and $N^6$ methyladenine modified DNA.

Restriction of *E. coli*-streptomyces Shuttle Vectors is due to in vivo methylation

*E. coli* RR1, the host for the shuttle vectors in Table 2, contains two DNA methylases. The dcm product modifies the sequence GG(AT)CC to produce 5-methylcytosine and the dam product modifies the sequence GATC yielding $N^6$-methyladenine. As shown above, *S. avermitilis* restricts modified DNA, this could explain why *S. avermitilis* can not be transformed by shuttle vectors isolated from *E. coli* RR1. To test if the dcm and dam modifications cause *S. avermitilis* to restrict shuttle vectors isolated from *E. coli*, shuttle vectors were isolated from a methylase deficient *E. coli* GM272 (dcm,dam,hsd). As Table 5 shows, DNA from GM272 could be transformed directly into *S. avermitilis*. However, the plasmids isolated from GM272 still showed a reduced efficiency of transformation compared to plasmids isolated from Streptomyces. The residual restriction of DNA isolated from GM272 may be because the dam and dcm mutations in GM272 do not completely eliminate all DNA methylation. This was tested by comparing the restriction enzyme digestion pattern of shuttle vector DNA isolated from GM272 and Streptomyces which had been cleaved with methylation sensitive enzymes. When pVE3 and pVE328 DNAs isolated from GM272 were cleaved with MboI and EcoRII, faint bands resulting from only partial cleavage were visible. In contrast, the shuttle vectors DNAs isolated from Streptomyces were cleaved to completion. Thus, it is likely the restriction seen when DNA from GM272 is introduced into *S. avermitilis* is the result of the residual methylase activity in GM272.

Common Occurence of Methyl-Specific Restriction in Streptomyces

*S. avermitilis* is the first strain described which restricts DNA containing 5-methylyctosine or $N^6$-methyladenine. To determine if methyl-specific restriction was unique to *S. avermitilis*, nine Streptomyces were tested for methyl-specific restriction. These included eight other Streptomyces known to be hosts for pVE1 derivatives, and *S. cyanogriseus* which produce avermectin like compounds. Table 6 presents the methyl-specific restriction pattern of the nine Streptomyces successfully transformed by pVE28. As Table 6 shows, most of the strains tested (7/9) had a methyl-dependent restriction system. However, *S. avermitilis* was unique in restricting DNA modified at either A or C. Three strains only restricted $N^6$-methyladenine containing DNA and three strains only restricted 5-methylyctosine containing DNA Two strains showed no evidence of methyl-dependent restriction, *S. bikiniensis* and *S. fervens*.

*S. avermitilis* possess a unique methyl-specific restriction system. This system is responsible for the inability to move shuttle vectors from most *E. coli* strains directly into *S. avermitilis*. Using in vitro methylated plasmids, *S. avermitilis* was found to restrict DNA containing 5-methylyctosine or $N^6$-methyladenine modifications. The amount of restriction observed in *S. avermitilis* appears to be correlated with the number of modified sites in DNA. Plasmids with 1 to 3 methylated bases per molecule were only restricted about 10 fold, but plasmids with more than 10 methylation sites were restricted greater than 1000 fold (see Table 4). No evidence was found for sequence specificity, since plasmid DNA treated with each of the eight methylases tested (Table 4) was restricted by *S. avermitilis*. Restriction systems in Streptomyces are common, but this is the first description of a methyl-specific restriction system in Streptomyces. Some bacteria methylate DNA to produce $N^4$-methylycytosine Butkus et. al., *Nucleic Acids Res.* 13 5727-5746 (1985). It is not known, but certainly possible, that the *S. avermitilis* restriction system is sensitive to this form of modification.

Two other bacteria, *E. coli* Raleigh et. al., *Proc. Nat Acad Sci USA* 83 9070-9074 (1986) and *Acholeplasma laidlawaii* Sladok et. al., *J. Bacterial* 165 219-225 (1986) are known to restrict DNA containing 5-methylcytosine with little or no sequence specificity. In *E. coli*, two distinct genetic loci have been correlated with 5-methylcytosine specific restriction. One loci mcrB restricts DNA methylated with many, but not all methylases tested and may recognize the sequence GmC or RmC. A second loci, mcrA, only restricts DNA methylated by the HpaII methylase at the site CmCGG. In *A. laidlawaii* restriction was observed when DNA was modified with any of five 5-methylycytosine specific methylases tested and no sequence specificity was observed. Several bacteria, notably, *Diplococcus pneumoniae* Lacks et. al., *J. Mol Biol* 114 153-168 (1977) contain a sequence specific, $N^6$-methyladenine- specific restriction system. This system restricts DNA containing GmATC. The GmATC modification is a result of dam methylases, which are common in Enterobacteriaceae and Haemophilus. *S. avermitilis* is unique in that it restricts both 5-methylyctosine and $N^6$-methyladenine modified DNA, with no apparent sequence specifity. However, as shown by Table 6, methyl-specific restriction is common in the Streptomyces strains tested. Seven of the nine strains that could be transformed by pVE28 possess methyl specific restriction systems.

The methyl specific restriction system of *S. avermitilis* prevents the direct introduction of shuttle vectors grown in *E. coli* (Table 2), as well as DNA isolated from other bacteria that modify DNA (Table 3). This restriction barrier can be overcome by passage of DNA through non-methylating hosts such as *S. lividans* (Tables 2, 3, and 5) or by passage through methylase deficient *E. coli* GM272 (Table 5). However, both strains are not optimal intermediates for the process described here. *S. lividans* expresses a weak methyl specific restriction system (Table 2) and *E. coli* GM272 expresses low level methylation activity which results in restriction by *S. avermitilis* (Table 5). S. fervens, which lacks all detectable methyl-specific restriction, is a preferable intermediate host. With an understanding of the restriction system of *S. avermitilis* many of the cloning techniques developed in *E. coli* can now be applied to *S. avermitilis* by using suitable shuttle vectors.

Recombinant plasmids containing cloned genes have many experimental uses. With such a rich source of the purified gene, it is possible to perform a detailed genetic and physical analysis of the gene to identify regulatory regions and the coding region for the structural gene. The DNA sequence of the gene or portions of it can be determined. If a gene of interest has been cloned into a vector which is a bifunctional replicon, such as pVE3 which replicate in both *E. coli* and Streptomyces, many additional experiments are then possible. Because of the thorough genetic characterization of *E. coli*, vectors such as pVE3 enable one to perform a variety of in vivo genetic manipulations in *E. coli* that are not yet possible in Streptomyces.

Recombinant plasmids containing cloned genes can be reintroduced into the wild type host organism to determine the effect of high copy number of a gene in the biosynthetic pathway of the secondary metabolite. For example, if the rate limiting step in a pathway has been cloned, supplying this gene in many copies per cell may greatly increase the yield of the metabolite. If several or all of the genes of a particular metabolic pathway have been cloned, it may be possible to construct in vitro a single plasmid containing the complete pathway. This would allow an increase in the gene dosage of all steps involved and perhaps thereby increase the productivity of the strain.

The cloned gene can be manipulated in vitro in a variety of ways to increase the level of its expression. In vitro mutagenesis of the DNA presumably yields mutants with both positive and negative effects on the expression of the gene. Control sequences, such as high level promotors, can be introduced at the appropriate site next to the cloned gene to increase its level of expression. The effect of all alterations is monitored by reintroducing the altered cloned gene into the host Streptomyces.

The process of the instant invention involves the incorporating of DNA from a source which normally will not be incorporated into a Streptomyces microorganism, such as plasmid DNA derived from *E. coli*, strain RR1 and incorporating that plasmid DNA first into an intermediate host, such as *S. lividans* or *S. fervens*, or *E. coli* strain GM272 and then removing the plasmid DNA from the intermediate host and incorporating it in the usual manner into the desired Streptomyces microorganisms. It will be surprisingly observed that the restriction mechanism of the Streptomyces will not function in the expected manner and prevent the incorporating of the plasmid DNA, but will allow the plasmid DNA to become part of the genetic makeup of the Streptomyces. In such a manner the Streptomyces will be able to incorporate nucleic acid and enable it to perform functions which would not otherwise be possible such as yield improvement, the production of novel compounds, resistance to heat or other stresses, and the like.

The specific steps of the process of this invention are:

A. Identify a strain lacking all restriction systems which can serve as the intermediate host for the vector of step B.

B. Construct a vector which can replicate in the strain of step A.

C. Cleave the vector with an appropriate restriction enzyme to yield a linear molecule D. Isolate DNA from the source organism from which genes will be cloned.

E. Cleave the DNA with restriction enzymes to generate fragments appropriate for the linear vector of step C.

F. Ligate the linear vector of step C with the cleaved DNA fragments of step E, and transform into the intermediate host of step A.

G. Select for a phenotype of the genes of interest andor the vector.

H. Isolate the recombinant DNA from the intermediate host of step A.

I. Transform the recombinant DNA of step H into the target microorganism.

J. Select for a phenotype of the vector or genes of interest andor the vector.

In step A above, since many Streptomyces possess methyl-specific restriction systems, it is most advantageous to select as the intermediate host organism one which lacks such methyl-specific restriction systems. Specific examples that have been found useful intermediates for transferring normally restricted systems into such methyl-restricted Streptomyces are *S. lividans, S. fervens* and *E. coli* GM272.

In steps B and C the vector which is to be incorporated into the target organism is constructed. Such a vector will generally be for the purposes of improving a particular characteristic of the target organism or for the purposes of imparting a property into the target organism which is not present in such target organism. Specific examples are the Streptomyces-*E. coli* shuttle vectors PVE3 and PVE328.

In steps D, E and F DNA fragments from the source organism, generally a Streptomyces encoding the production interesting compounds are isolated. These fragments, following well established procedures will allow for the transfer of genetic material from the source organism to the intermediate host The ligation step F, joins the DNA with the vector which the DNA will be able to be incorporated into the intermediate host, bringing the vector along with it.

When the intermediate host is cultured, the vector which had been incorporated therein or part of its genetic material is cultured also and the intermediate host can be selected for the phenotype of the genes which contain the vector produced in steps B and C.

When the selected recombinant DNA is removed from the intermediate host culture it can be incorporated into the target organism using the same techniques used to produce the intermediate host culture. This genetic material will not be restricted from the target culture as would be expected since the original DNA isolated from the source culture would have been restricted and would not have been incorporated into the target organism. Thus, the process of this invention accomplishes with facility that which is not otherwise possible.

The occurrence of methyl-specific restriction systems in Streptomyces, as well as *E. coli* and *A. laidlawaii* demonstrates that this form of restriction is wide spread in bacteria. Methyl-specific restriction will make the development and use of cloning systems difficult in many bacteria.

The plasmid pVE328 has been made available to the public as a deposit of the culture *Escherichia coli* in a strain identified as ET 11,887, MB5331. This strain has been deposited for patent purposes with the American Type Culture Collection, 12301 Parklawn Drive, Rockville, Md., 20852 and has been given the accession number ATCC 67698. The same culture has been deposited under the Budapest Treaty on the International Recognition of the Deposit of Microoganisms for the Purpose of Patent Procedure and has been given the accession number ATCC 68408.

The following examples are provided in order that the invention might be more fully understood. They should not be considered as limitative of the invention.

EXAMPLE 1

Isolation, Maintenance, and Propagation of Plasmids

The plasmid DNA was isolated and handled by procedures differing little from those established by work on other plasmids. A good procedures manual is T. Maniatis, E. F. Fritsch, and J. Sambrook, "Molecular Cloning: a Laboratory Manual," Cold Spring Harbor Laboratory, Cold Spring Harbor, N.Y. (1982). A good procedures manual for Streptomyces is D. A. Hopwood, M. J. Bibb, K. F. Chater, T. Kieser, C. J. Bruton, H. M. Kieser, D. J. Lydiate, C. P. Smith, J. M. Ward, and H. Schrempf, "Genetic Manipulation of Streptomyces, a Laboratory Manual," John Innes Foundation, Norwich, UK (1985). The specific procedures used in this work are described herein, unless they are identical to those given in the above mentioned manuals.

A. Growth of Streptomyces for Plasmid Isolation

Single colonies of Streptomyces strains were isolated on R2YE or YME-TE media. R2YE contained 103 g sucrose, 10 g glucose, 3 g yeast extract, 3 g proline, 0.1 g casamino acids, 0.25 g $K_2SO_4$, 10.1 g $MgCl_2.6H_2O$, 2 ml of R2 trace elements (0.2 g $FeCl_3.6H_2O$, 0.04 g $ZnCl_2$, 0.01 g $MnCl_2.4H_2O$, 0.01 g $CuCl_2.2H_2O$, 0.01 g $NaB_4O_7. 10H_2O$, and 0.1 g $(NH4)_6Mo_7O_{24}.4H_2O$ per liter) and 15 g agar per liter. After autoclaving, the following solutions were added to each liter of medium: 10 ml of 0.5% $KH_2PO_4$, 8 ml of 2.5M $CaCl_2$, and 40 ml of 0.2M TES pH 7.2 (N-tris (hydroxymethyl) methyl-2-amino ethanesulfonic acid). YME-TE contained 4 g yeast extract, 10 g malt extract, 4 g glucose, 5 ml of YME trace elements (50 ml of 37.3% HCl, 61.1 g $MgSO_4.7H_2O$, 2 g $CaCO_3$, 5.4 g $FeCl_3.6H_2O$, 1.44 g $ZnSO_4.7H_2O$, 1.11 g $MnSO_4.H_2O$, 0.25 g $CuSO_4.5H_2O$, 0.062 g $H_3BO_3$ and 0.49 g $Na_2MoO_4.2H_2O$ per liter), and 15 g agar per liter. The pH of YME-TE was adjusted to ph 7.0 with NaOH before autoclaving.

Liquid growth medium for Streptomyces was YEME (3 g yeast extract, 5 g peptone, 3 g malt extract, 10 g glucose per liter) modified to contain 30% sucrose, 5 mM $MgCl_2$ and included antibiotics to select for the maintenance of plasmids. Strains with plasmids containing a thiostrepton-resistance gene (tsr) were grown with 5 μg per ml of thiostrepton and strains containing a plasmid with a neomycin-resistance gene (neo) were grown with 10 μg per ml of neomycin. A single colony was inoculated into 6 ml of YEME in a 18 mm by 150 μmm tube. The culture was grown for 3 days at 28° C. with shaking at 220 rpm.

(1) Small scale plasmid isolation

For small scale plasmid preparations mycelia from the 6 ml YEME culture was collected by centrifugation at 14,000×g for 12 minutes. The pellet was washed once in 10% sucrose, 10 mM ethlenediamino teraacetate (EDTA), pH 8.0. Plasmid DNA was isolated form the mycelia by a rapid boiling procedure described previously by MacNeil, D. J., J. of *Microbiol. Methods* 5 pg 115-123, (1986). The pellet was resuspended in 0.5 ml of STET (8% sucrose, 5% Triton X-100, 50 mM EDTA and 50 mM Tris, pH 8.0), 30 μl of a 30 mg/ml lysozyme solution was added, the mixture was incubated for 15 minutes at 37° C., and then placed in a boiling water bath for 2 minutes. The boiled lysate was spun at 14,000×g for 12 minutes, the supernatant was removed to an 1.5 ml Eppindorf tube, and then extracted once with phenol previously equilibrated with TE 10 mM Tris, 1 mM EDTA, pH 7.9). The aqueous phase was removed to another 1.5 ml Eppindorf tube, an equal volume of isopropanol was added, the solutions were incubated at −20° C. for 20 minutes, and the DNA was pelletted at 7000×g for 6 minutes. After washing once in 70% ethanol, the DNA was resuspended in 100 μl of TE. An estimated 2 to 10 μg of plasmid DNA was obtained from a 6 ml culture.

(2) Large scale plasmid isolation

For large scale plasmid isolations a 6 ml YEME culture was used to inoculate a 250 ml baffled flask containing 30 ml of YEME. After 2 days shaking at 28° C. at 220 rpm the culture was used to inoculate a baffled 2 liter flask containing 500 ml of YEME. The mycelia was harvested by centifugation at 14,000×g for 15 minutes and was washed once in 10% sucrose, 10 mM EDTA. Plasmid DNA was isolated from the mycelia by a rapid boiling procedure as described previously by MacNeil, D. J., 1986, supra. The cell pellet was resuspended in 40 ml of STET, 0.5 ml of 50 mg/ml lysozyme solution in 0.1M Tris pH 7.9 was added. The suspension was incubated at 37° C. for 20 minutes, placed in a boiling water bath for 3 minutes and centrifuged at 90,000×g for 30 minutes at 4° C. The supernatant was removed, one half volume of −20° C. isopropanol was added, mixed and incubated at 20° C. for 20 minutes. DNA was collected by centrifugation at 9000×g for 8 minutes. The DNA was resuspended in 13 ml of a CsCl solution prepared by dissolving 78g of CsCL into 65 ml of 0.1M Tris, 0.01M EDTA, pH 7.9 and adding 2 ml of ethidium bromide (5 mg/ml). The mixture was centrifuged at 43000 rpm in a Beckman ultracentrafuge for 44 hours. The plasmid DNA band was removed and rebanded in 13 ml of a CsCl solution prepared by dissolving 71 g of CsCL into 65 ml of 0.1M Tris, 0.01M EDTA, pH 7.9 and adding 2 ml of ethidium bromide (5 mg/ml). The plasmid DNA was removed from the second gradient and ethidium bromide was removed by 4 isopentyl alcohol extractions. The plasmid DNA was precipitated by adding 2 volumes of TE, 0.3 volumes of 3.5M sodium acetate, and 6 volumes of 100% ethanol. After overnight incubation at −20° C. the DNA was pelleted by cetrifugation at 13000×g for 12 minutes, washed once with 70% ethanol, and resuspended in 1 ml of TE. The yield of DNA from 500 ml of cells was 200 to 500 μg.

B. Growth of *E. coli* for plasmid isolation

*E. coli* cultures containing pVE3 and pVE328 were grown in LB-Amp medium (10 g tryptone, 5 g yeast extract, 5 g NaCl per liter containing 75 μgml of ampicillin). These cultures were grown overnight at 37° C. shaking at 220 rpm. Small scale plasmid preparations were prepared from the 5 ml of culture by the rapid boiling method of Holmes, D. S. and Quigley, M., *Anal. Biochem.* 70 pg 431-441 (1981). Plasmid DNA was isolated as described above for Streptomyces except the cells were pelleted at 6000×g for 5 minutes, resuspended in 0.4 ml of STET, and 30 μl of a 10 mg/ml lysozyme solution was added. Large amounts of plasmid DNA (200 to 800 μg) were prepared from a 500 ml culture by the Triton X-100 cleared lysate method of Clewell, D. B. and Helinski, D. R., *Proc. Natl. Acad. Sci. USA,* 62 pg 1159-1166 (1969). 500 ml cultures were prepared by inoculating 500 ml of LB-Amp medium with 1 ml of an LB-amp overnight culture and incubating the culture overnight at 37° C. with shaking at 220 rpm. Cells were collected at 8000×g for 8 minutes, resuspended in 5 ml of 25% sucrose, 50 mM Tris pH 8.0, and 1 ml of a lysozyme solution (10 mg/ml in 0.1M Tris pH 7.9) added. After 10 minutes on ice 1.5 ml of 0.5M EDTA was added, mixed and incubated on ice 10 minutes. Cells were lysed by the addition of 9 ml of 10% Triton X-100, 0.05M Tris, 0.06M EDTA, pH 8.0 The lysate was centrifuged at 40K for 50 minutes in a Beckman ultracentrafuge. The nonviscous supernatant was transferred to a new tube, one half volume of −20° C. isopropanol was added, mixed and incubated at −20° C. for 20 minutes. DNA was collected by centrifugation at 9000×g for 8 minutes. The DNA was resuspended in 13 ml of a CsCl solution prepared by dissolving 78g of CsCl into 65 ml of 0.1M Tris, 0.01M EDTA, pH 7.9 and adding 2 ml of ethidium bromide (5 mg/ml). The mixture was centrifuged at 43000 rpm in a Beckman ultracentrafuge for 44 hours. The plasmid DNA band was removed and rebanded in 13 ml of a CsCl solution prepared by dissolving 71 g of CsCl into 65 ml of 0.1M Tris, 0.01M EDTA, pH 7.9 and adding 2 ml of ethidium bromide (5 mg/ml). The plasmid DNA was removed from the second gradient and ethidium bromide was removed by 4 isopentyl alcohol extractions. The plasmid DNA was precipitated by adding 2 volumes of TE, 0.3 volumes of 3.5M sodium acetate, and 6 volumes of 100% ethanol. After overnight incubation at −20° C. the DNA was pelleted by centrifugation at 13000×g for 12 minutes, washed once with 70% ethanol, and resuspended in 1 ml of TE.

C. Restriction analysis of plasmid DNA

Procedures for restriction analysis of DNA and agarose gel electrophoresis as well as other standard techniques of recombinant DNA technology are thoroughly described in the useful manual T. Maniatis, E. F. Fritsch, and J. Sambrook, "Molecular Cloning: a Laboratory Manual," Cold Spring Harbor Laboratory, Cold Spring Harbor, N.Y. (1982).

Figure 1:
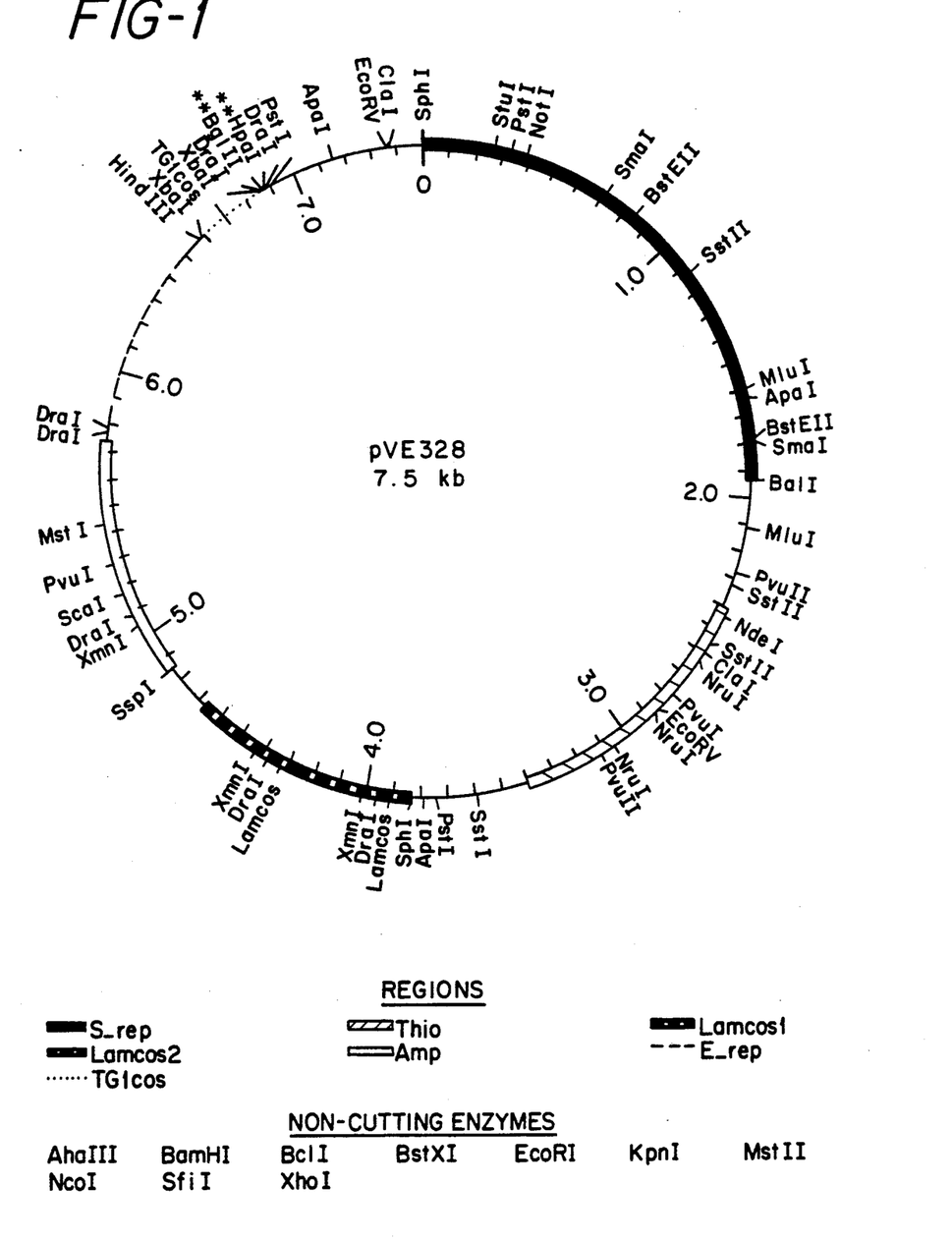

Plasmid DNA isolated from large and small scale preparations were cleaved with SstII and analyzed by electrophoresis in 0.8% agarose using 0.08M Tris-acetate-0.004M EDTA as a buffer. The size of the fragments was determined by comparison to fragments of phage lambda DNA of known molecular weight. The restriction maps of plasmids pVE3, pVE28 and pVE203 were determined previously (MacNeil, T. and Gibbons, P. H., Plasmid 16 pg 182-194 (1986). A restriction map of pVE328 is shown in FIG. 1.

D. Transformation of Streptomyces by plasmid DNA (1) Protoplast formation.

Transformation was accomplished by PEG-mediated DNA uptake by protoplasts. Protoplasts of *S. avermitilis* were prepared as described by MacNeil, D. J. and Klapko, L. M., 1987, J. Indust. Microbiol 2:209–218. 30 ml of YEME medium were inoculated with $5 \times 10^7$ spores of *S. avermitilis*, grown for 3 days at 28° C., the mycelium was pelleted at $14000 \times g$ for 12 minutes, washed once with P medium (Okanishi, M., Suzuki, K. and Umezawa, H., 1974, J. Gen, Microbiol. 80:389–400). P medium contained 103 g sucrose, 0.25 g $K_2SO_4$, 2.03 g $MgCl_2.H_2O$, and 2 ml of R2 trace elements per liter. After autoclaving the following additions were made: 10 ml of 0.5% $KH_2PO_4$, 8 ml $CaCl_2.2H_2O$, 40 ml of 0.2M MES (2-(N-morpholino) ethanesulfonic acid). The mycelium was resuspended in 15 ml of P medium, 0.2 ml of lysozyme (50 mg/ml in P medium) was added, and the suspension was incubated at 37° C. for 1 hour with slow shaking. Protoplasts were separated from undigested mycelium by filtering the mixture through 2 cm of glass wool in the bottom of a 10 ml syringe. The protoplasts were pelleted at $6000 \times g$ for 6 minutes and resuspended in 3 ml of P medium which contained 20% sucrose. Protoplasts of *S. lividans* were prepared as described above for *S. avermitilis*, except TES was used in all buffers instead of MES. Protoplasts of other Streptomyces listed in Table 6 were prepared as described for *S. avermitilis* except the buffer used to prepare and store protoplasts was a modified P medium. Modified P medium was made by adding 20 ml of 0.2M MES and 20 ml of 0.25M TES in place of 40 ml of MES. All protoplasts were quick frozen in a dry ice/ethanol bath and stored at −70° C.

(2) Transformation procedure

Streptomyces strains were transformed by a modification of the method described for *S. avermitilis* (MacNeil and Klapko, 1987, supra). 0.1 ml of protoplasts (approximately $10^9$/ml) were mixed with 10 μl of plasmid DNA (10 μg/ml), 0.5 ml of medium T was added and the mixture incubated for 30 seconds at room temperature. Medium T is similar to P medium except it contains different concentrations of sucrose (2.5%), $CaCl_2$ (0.1M) and is buffered with 50 mM Tris-maleic acid (pH 8) and has 25% (wt/vol) PEG 1000. The mixture was serially diluted in P medium containing both 0.01M MES and 0.01M TES. For *S. bikiniensis, S. coelicolor, S. fervens, S. griseus, S. griseoplanus, S. lividans,* and *S. parvulus* 100 μl of the dilutions of the transformation mixtures were spread on R2YE medium containing 17% sucrose. For *S. avermitilis, S. cyanogriseus,* and *S. rochei* 100 μl of the dilutions of the transformation mixtures were added to 3 ml of RM14 soft agar at 50° C. and poured onto RM14 plates. RM14 is similar to R2YE except it contains 205 g sucrose, 20 g agar, an additional 3 g of oatmeal agar per liter, and 0.1M MES instead of TES. RM14 soft agar contains only 6 g of agar per liter.

(3) Detection of transformation

R2YE and RM14 regeneration media containing the transformed protoplasts were incubated for 20 hours at 28° C. For plasmids which contain a tsr gene (pVE3, pVE28, pVE328, pVE614), regeneration plates were overlayed with 3 ml of RM14 soft agar containing 0.5 mg of thiostrepton. For pVE203 which contained a neo gene, regeneration plates were overlayed with 3 ml of RM14 containing 1.5 mg of neomycin. Transformants appeared on the regeneration plates in 4 to 15 days.

E. Transformation of *E. coli* by plasmid DNA

Competent cells of *E. coli* were prepared by the method of Mandel, M. and Higa, A., J. Mol. Biol., 53 pg 154-162 (1970). Cells were grown in LB medium to an $A_{600}=0.45$ and incubated on ice 20 minutes. Cells were pelleted and resuspended to one-half their original volume in 0.1M $CaCl_2$. After 20 minutes on ice, cells were again pelleted and resuspended to 0.1 of their original volume in 0.1M $CaCl_2$. These competent cells made 15% glycerol and stored at −70° C.

For transformations, 0.2 ml of competent cells was mixed with 10 μl of DNA (10 μg/ml). The mixture was incubated on 2 minutes at 37° C. and then 1 hour on ice. 0.5 ml of LB medium was added and the culture was shaken at 37° C. at 220 RPM for 1 hour. Aliquots were plated on LB plates with 75 μg/ml of ampicillin to select for the plasmids.

EXAMPLE 2

Construction of a *E. coli* lambda cosmid-Streptomyces TG1 cosmid shuttle vector The availability of a process to introduce DNA from *E. coli* into *S. avermitilis* makes the use of shuttle vectors possible. A useful shuttle vector is an *E. coli* cosmid-Streptomyces shuttle vector. Such a vector can be used to preferentially clone large segments of Streptomyces DNA. Since the genes for many antibiotics produced by Streptomyces have been found to be clustered, this kind of a shuttle vector can be used to clone an entire cluster of genes involved in antibiotic synthesis. FIG. 1 presents a restriction map of pVE328, a cosmid vector which can replicate in *E. coli* conferring ampicilin-resistance (Amp$^r$) and Streptomyces conferring Thio$^r$. pVE328 is only 7.5 kb in size so it can clone DNA fragments up to 43 kb, and pVE328 contains two lambda cos sites so it can be efficiently packaged into phage heads in vitro. pVE328 also contains unique BglII and HpaI cloning sites flanked by DraI sites. The BglII cloning site allows the incorporation of fragments with GATC ends, which are produced by BamHi, BglII, BclI, XhoII, and MboI. The HpaI site can be used to clone blunt ended fragments. Since Streptomyces DNA was a high G+C ratio, often greater than 70%, the DraI site TTTAAA is very rare (1 per 300 kb). Thus, most fragments cloned into the BglII or HpaI sites can be excised with DraI for further analysis and manipulation. Finally the vector contains the broad host range Streptomyces phage TG1 cos site. This site can be used in vivo by TG1 helper phage to package pVE328 derivatives into TG1 virions. A TG1 lysate grown on a pVE328 derivative can then be used to introduce the pVE328 derivatives into other Streptomyces by phage mediated transduction. This technique is technically simpler than transformation and expands the hosts into which the clone may be introduced.

pVE328 was constructed using standard recombinant DNA technology differing little from the procedures in Maniatis et al., supra. Up to 5 μg of vector or insert DNA was digested in 100 μl of KC1 buffer (20 mM Tris, 20 mM KC1, 10 mM MgCl$_2$, 1 mM Dithiothreitol, pH 8) for 2 to 4 hours with 2U of restriction enzyme per μg of DNA. Reactions were terminated by heating for 15 minutes at 65° C. followed by phenol extraction. The DNA in the aqueous phase was made 0.25M sodium acetate, 2 volumes of ethanol were added, the DNA was precipitated at −70° C. for at least 1 hour, pelleted at 14,000×g, and resuspended in 20 μl of TE. All ligations were performed in 20 μl reaction volumes containing 0.2 to 0.5 μg of vector and a 3 fold molar excess of insert DNA. Ligations were performed using New England Biolabs T4 DNA ligase in 1 x ligation buffer (50 mM Tris, 10 mM MgCl$_2$, 20 mM dithiothreitol, 1 mM ATP, 50 μg bovine serum albumin) and incubated at least 16 hours at 12° C. Recombinant molecules were transformed into E. coli RR1 selecting (Amp$^r$). Small scale preparations of plasmid DNA were prepared from the transformants and analyzed with restriction enzymes to identify plasmids with the expected restriction pattern.

The starting plasmid was pSVO10X2 obtained from Rick Myers via F. Foor. pSVO10X2 is a deletion derivative of pBR322 which contains two multiple cloning regions and some SV40 DNA. A derivative of pSVO10X2 which contained a single multiple cloning region and lacked the SV40 DNA was isolated after a complex ligation. This ligation involved two digestions of pSVO10X2 (one with PstI, HindIII and PvuI and the other with BamHI, HindIII and PvuI), and the digestion of pMC1403 (obtained from M. Casadaban, University of Chicago), with BamHI, PstI, and PvuII. Among the products of this ligation was a 2 kb plasmid, designated pVE61, that was found to have a multiple cloning region containing sites for the enzymes EcoRI, SmaI, BamHI, PstI, BglII, XbaI, and HindIII. This plasmid was converted to an E. coli lambda cosmid by addition of 405 bp HincII cos fragment from pVE81, into the unique SmaI site of pVE61 to yield pVE105. The cos region in pVE81 had been previously cloned as a 3.2 kb EcoRI-BglII fragment from lambda into the EcoRI-BamHI sites of pBR322 to yield pVE81. The PstI site in the amp gene of pVE105 was removed by substituting the BglI to AatII fragment of pUC8 (Bethesda Research Laboratories, Gaithersburg, MD) for the BglI to AatII fragment of pVE105 to yield pVE163. This cosmid was made into a shuttle cosmid by ligation of the Streptomyces plasmid pVE95 to pVE167. pVE95 is a stable, thio$^r$ deletion derivative of pVE28 isolated after digestion of pVE28 with SstI and subsequent ligation. pVE95 was linearized at its unique BglII site and ligated to pVE163 linearized at its unique BamHI site to yield pVE167. Unique cloning sites were introduced into pVE167, linearized at its BglII site by the ligation of a synthetic oligonucleotide of sequence:

GATCGTTTAAAGTTAACAGATCTTTAAAG
    CAAATTTCAATTGTCTAGAAATTTCCTAG The double strand oligonucleotide was prepared by mixing together 10 μg of each single stranded 29 mer in 50 μl of TE, the mixture was heated to 85° C. for 5 minutes, slowly cooled to room temperature and stored overnight at 4° C. One half microgram of pVE167 was mixed with a 50 fold molar excess of annealed oligonucleotide and ligated with T4 DNA ligase. Among the Amp$^r$ transformants, an isolate containing a single copy of the oligonucleotide was identified and designated pVE232. pVE232 was converted into a Streptomyces phage TG1 cosmid by addition of a 270 bp EcoRV-HpaI fragment containing the TG1 cos site. pVE232 was linearized at its XbaI site, the site made blunt by treatment with DNA polymerase Klenow fragment (Bethesda Research Laboratories, Gaithersburg, Md.), and ligated to TG1 cleaved with HpaI and EcoRV. pVE288 was identified as derivative which contained the 270 bp cos fragment. The TG1 cos fragment can be cleaved from pVE288 with XbaI since insertion of the HpaI-EcoRV fragment into the filled in XbaI site regenerated two XbaI sites. A second lambda cos site was inserted into a pVE288 after it was digested with EcoRI and treated with DNA polymerase Klenow fragment. The resulting blunt-ended linear molecule of pVE288 was ligated to pVE81 digested with HincII and a derivative with two lambda cos sites in the same orientation was identified and designated pVE328. The two primary cloning sites, BglII and HpaI, are indicated by ** in FIG. 1. Other unique sites in the plasmid that could be used for cloning and which do not interfere with any plasmid functions are the HindIII, BalI, and SstI sites.

EXAMPLE 3

Cloning the avermectin genes

Avermectins are complex macrolide compounds highly active agents useful in the control of human and animal parasites and agricultural pests. The enzymes required to synthesize the avermectins are encoded by many genes. Once cloned, the avermectin genes could be used to improve the titer and component ratio of avermectins. In order to clone all the genes a vector is required which can accept a large chromosomal insert. Such a vector is an E. coli cosmid vector which can clone fragments up to 40 kb. To directly test clones derived from the insertion of S. avermitilis DNA into a cosmid vector it is necessary to transfer the cosmids from E. coli to Streptomyces. One such cosmid is pVE328 which contains two lambda cos sites for in vitro packaging in E. coli; a pBR322 replication region and amp gene for selection in E. coli; and a pVE1 replication region and tsr gene for selection in Streptomyces. Any E. coli-Streptomyces shuttle vector which can be packaged by lambda would also function for this purpose. pVE328 was linearized with BglII and treated with calf alkaline phosphatase (CIAP), in order to maximize the frequency of inserts within the vector. S. avermitilis chromosomal DNA was partially digested with Sau3A and fragments in the size range 30 to 40 kb isolated from a sucrose gradient centrifugation. These enzymes generate the same 5'4 base extension. The fragments and linearized vector were ligated together using T4 DNA ligase supplied by New England Biolabs and used according to their instructions. The ligation mixture was packaged into lambda phages with a Ambersham lambda in vitro packaging kit. A library of S. avermitilis DNA was made by transducing E. coli with packaged lambda lysate and selecting ampicillin resistance. DNA from the colonies can not be directly introduced into S. avermitilis because of methyl specific restriction.

However, using the process described here, the cosmid library DNA is transformed into *S. fervens*, transformants are isolated by selecting thiostrepton resistance, DNA is prepared and then introduced into *S. avermitilis* mutants defective in avermectin biosynthesis. Identification of clones which complement the defect can be made by testing thiostrepton resistant colonies for avermectin production. By subcloning the gene encoding the enzyme for the rate limiting step in avermectin biosynthesis onto a high copy number plasmid, higher titers of avermectin can be produced. The ratio of the 8 major natural avermectins can be changed by subcloning the ene(s) involved in avermectin synthesis, such as avermectin macrolide O-methyltransferase, or avermectin macrolide dehydrastase. New analogues of avermectin can be made by mutagenizing the cloned avermectin genes to alter their substrate specificity.

TABLE 5

TRANSFORMATION OF SHUTTLE VECTORS ISOLATED FROM A METHYLASE DEFICIENT E. coli

| DNA | Strain | Source of DNA Methylase | Transformation Frequency[1] in E. coli RR1 | S. avermitilis |
|---|---|---|---|---|
| pVE3 | E. coli RR1 | dam, dcm | $2 \times 10^3$ | <10 |
|  | E. coli GM272 | none | $2 \times 10^3$ | $2 \times 10^5$ |
|  | S. lividans | none | $2 \times 10^3$ | $3 \times 10^5$ |
| pVE328 | E. coli RR1 | dam, dcm | $2 \times 10^4$ | <10 |
|  | E. coli GM272 | none | $2 \times 10^4$ | $4 \times 10^2$ |
|  | S. lividans | none | $2 \times 10^4$ | $4 \times 10^6$ |

[1]Number of transformants per 100 ng of DNA, results are the average of two experiments.

TABLE 6

TRANSFORMATION OF SEVERAL STREPTOMYCES WITH METHYLATED PVE28

| Strain | Transformants[1] Untreated | Relative Transformation Frequency[2] Methylase Treatment | | | |
|---|---|---|---|---|---|
|  |  | dam GmATC | TaqI TCGmA | AluI AGmCT | HhaI GmcGC |
| S. avermitilis | $2 \times 10^6$ | .0002 | .0002 | .001 | .0002 |
| S. bikiniensis | $3 \times 10^5$ | 1 | 1 | 1 | 1 |
| S. coelicolor | $3 \times 10^6$ | .02 | .02 | 1 | 1 |
| S. cyanogriseus | $3 \times 10^5$ | 1 | 1 | .0003 | .0003 |
| S. fervens | $5 \times 10^6$ | 1 | 1 | 1 | 1 |
| S. griseoplanus | $4 \times 10^5$ | .005 | .001 | 1 | 1 |
| S. lividans | $2 \times 10^6$ | .3 | .4 | 1 | 1 |
| S. parvulus | $2 \times 10^6$ | 1 | 1 | .0005 | .001 |
| S. rochei | $9 \times 10^5$ | 1 | 1 | .0002 | .001 |

[1]Number of transformants per 100 ng of pVE28 DNA, results are the average of two experiments.
[2]Relative transformation frequency =
Number of transformants with 100 ng of methylated pVE28 divided by
Number of transformants with 100 ng of untreated pVE28

TABLE 7
References

1. Bolivar, et al., Gene 2:95-114 (1977).
2. Burg, et al., Antimicrob. Agents Chemother. 15:361-367 (1979).
3. Clewell, et al., J. Bacteriol. 110:1135-1146 (1972).
4. Cox, et al., J. Bacteriol 159:499-504 (1984).
5. Fisher et al., In S. Omura (ed.), Macrolide Antibiotics Academic press, Orlando, FL. (1984)
6. Foor, et al., Gene 39:11-16 (1985)
7. Floss et al., Trends in Biotechnol 5:111-115 (1987).
8. Hershbeger, et al., European Patent Application 86-089339.
9. Holmes, et al., Analyt. Biochem. 114:193-197 (1981).
10. Hopwood, et al., Nature 314:642-644 (1985).
11. Hopwood, et al., Genetic manipulation of Streptomyces, a Laboratory Manual, John Innes Foundation, Norwich, UK (1985).
12. Kessler, et al., Gene 47:1-153 (1986).
13. Kieser, et al., Mol. Gen. Genet. 185:223-228 (1982).
14. MacNeil, et al., J Microbiol. Meth. 5:115-123 (1986).
15. MacNeil, et al., J. Indust. Microbiol. 2:209-218 (1987).
16. MacNeil, et al., Plasmid 16:182-194 (1986).
17. Maniatis, et al., Molecular Cloning: A Laboratory Manual. Cold Spring Harbor Laboratory, Cold Spring Harbor, N.Y. (1982).
18. Mandel, et al., J. Mol. Biol. 53:154-162 (1970).
19. Matsushima, et al., Mol. Gen. Genet. 206:393-400 (1987).
20. Miller, Experiments in Molecular Genetics. Cold Spring Harbor Laboratory, Cold Spring Harbor, N.Y. (1972).
21. Okanishi, et al., J. Gen. Microbiol 80:389-400 (1974).
22. Omura, "Macrolide antibiotics: chemistry biology, practice", Academic Press, Orlando (1984).
23. Putter, et al., Experientia 37:963-964 (1981).
24. Roberts, et al., Nucleic Acids Res. 13:r165-r200 (1985).
25. Thompson, et al., Gene 20:51-62 (1982).
26. Thompson, et al., J. Bacteriol 151:668-677 (1982).

What is claimed is:
1. Plasmid pVE328.

* * * * *